(12) United States Patent
Bonney et al.

(10) Patent No.: US 6,752,145 B1
(45) Date of Patent: Jun. 22, 2004

(54) MEDICATION DISPENSER

(75) Inventors: Stanley George Bonney, Ware (GB); Anthony Patrick Charles Jones, Ware (GB); Duncan Robertson, Ware (GB)

(73) Assignee: Smithkline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/979,485

(22) PCT Filed: Apr. 19, 2000

(86) PCT No.: PCT/EP00/03519

§ 371 (c)(1),
(2), (4) Date: Nov. 19, 2001

(87) PCT Pub. No.: WO00/69496

PCT Pub. Date: Nov. 23, 2000

(30) Foreign Application Priority Data

May 18, 1999 (GB) .............................. 9911388

(51) Int. Cl.[7] .............................. A61M 11/00
(52) U.S. Cl. .............................. 128/200.23; 128/203.12
(58) Field of Search ........................ 128/200.12, 200.14, 128/200.23, 200.24, 905, 203.12, 203.15, 203.14; 600/538; 222/36, 38, 23, 41, 45, 49

(56) References Cited

U.S. PATENT DOCUMENTS

| | | | |
|---|---|---|---|
| 3,789,843 A | | 2/1974 | Armstrong et al. |
| 4,414,972 A | | 11/1983 | Young et al. |
| 4,984,158 A | * | 1/1991 | Hillsman ............... 128/200.14 |
| 5,060,643 A | * | 10/1991 | Rich et al. ............. 128/200.23 |
| 5,133,343 A | * | 7/1992 | Johnson et al. ........ 128/200.23 |
| 5,284,133 A | * | 2/1994 | Burns et al. ............ 128/200.23 |
| 5,794,612 A | * | 8/1998 | Wachter et al. ........ 128/200.23 |
| 5,826,571 A | | 10/1998 | Casper et al. |
| 5,904,139 A | * | 5/1999 | Hauser .................. 128/200.23 |
| 5,957,125 A | * | 9/1999 | Sagstetter et al. ..... 128/200.23 |
| 6,155,251 A | * | 12/2000 | Hauser .................. 128/200.23 |
| 6,358,058 B1 | * | 3/2002 | Strupat et al. ............... 434/262 |
| 2003/0075171 A1 | * | 4/2003 | Jones et al. ............ 128/200.23 |
| 2004/0011357 A1 | * | 1/2004 | Braithwaite ............ 128/200.23 |

FOREIGN PATENT DOCUMENTS

| | | |
|---|---|---|
| EP | 441643 | 8/1991 |
| EP | 476991 | 3/1992 |
| EP | 490797 | 6/1992 |
| GB | 2263873 | 8/1993 |
| GB | 2264238 | 8/1993 |
| GB | 2292871 | 3/1996 |
| WO | 9213586 | 8/1992 |
| WO | 9619253 | 6/1996 |
| WO | 9841254 | 9/1998 |
| WO | 9847552 | 10/1998 |
| WO | 9906091 | 2/1999 |

* cited by examiner

*Primary Examiner*—Weilun Lo
*Assistant Examiner*—Teena Mitchell
(74) *Attorney, Agent, or Firm*—James P. Riek

(57) ABSTRACT

A dispenser for dispensing medicament comprising a housing; locatable within said housing, a container having a dispensing aperture, wherein said container is movable relative to the housing to enable dispensing therefrom; and an actuation-indicator for detecting movement of the container relative to the housing, said actuation-indicator comprising a first part defining a pocket having an outlet therefrom and a second part movable relative to said first part to create a pressure change at said outlet. The dispenser is suitable for dispensing medicament for the treatment of respiratory disorders.

19 Claims, 7 Drawing Sheets

MEDICATION DISPENSER

CROSS-REFERENCE TO RELATED APPLICATION

This is a U.S. National Phase filing under 35 USC 371. Priority is claimed from PCT/EP00/03519 filed Apr. 19, 2000, which claims priority from Patent Application GB 9911388.8 filed May 18, 1999 filed in the United Kingdom.

The present invention relates to an actuation recorder for recording the actuation profile of an inhalation device. In particular, the invention relates to an actuation recorder for use with a metered dose inhaler by means of which medicament contained in an aerosol container may be administered to a patient.

FIELD OF INVENTION

DESCRIPTION OF RELATED ART

It is well known to treat patients with medicaments contained in an aerosol, for example, in bronchodilator therapy. It is also known to use for such therapy, medicaments which are contained in an aerosol and are administered to a patient by means of an inhalation device comprising a tubular housing or sleeve in which the aerosol container is located and an outlet tube leading out of the tubular housing. The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the patient then holds the housing in a more or less upright condition and the mouthpiece or nozzle of the inhalation device is placed in the mouth or nose of the patient. The aerosol container is pressed towards the support to dispense a dose of medicament from the container which is then inhaled by the patient.

BRIEF DESCRIPTION OF THE INVENTION

It may be understood that effective delivery of medicament to the patient using an inhalation device as described above is to an extent dependent on the patient's ability to co-ordinate the actuation of the device (e.g. firing of the aerosol) with the taking of a sufficiently strong inward breath. The required co-ordination can present difficulties to some patients, with the risk that these patients do not receive the appropriate dose of medicament. It is, thus, desirable to provide a means for the patient to monitor their correct usage of the inhalation device. Such means might be designed for everyday usage or for use in a system for training patients in the correct usage of the inhalation device.

Various training systems have been described in the prior art. These typically involve the use of customised inhalers or apparatus incorporating or connected to various means for providing the patient with information about their correct (or incorrect) usage of the inhaler. Examples of such customised inhalers or apparatus include the inhaler described in WO93/12823 which incorporates various sensors and microprocessors; the inhalation apparatus described at U.S. Pat. No. 4,495,944 which includes various visual indicators to guide the patient; the biofeedback and training evaluation system described at U.S. Pat. No. 4,984,158; and the apparatus and visual display method described at U.S. Pat. No. 5,333,106.

A disadvantage associated with the use of such customised inhalers and apparatus is that the patient is trained with this customised equipment but then uses a standard inhalation device on a regular basis which is likely to have different shape, size, look and feel characteristics. In essence, therefore, the training system trains the patient to operate the customised equipment rather than their own inhalation device which they use regularly.

BRIEF DESCRIPTION OF THE INVENTION

The Applicants have now found that this disadvantage may be overcome by the use of an actuation-indicator and system which is employed as an add-on to a standard inhalation device. The patient may thus be trained in the use of a device which is identical to (or indeed is) the device they take home with them after the training session for everyday use.

Whilst the actuation-indicator of the present invention is connectable to electronic visual or audio display means, there is no requirement for any electrical connection on the device itself.

According to one aspect of the present invention there is provided a dispenser for dispensing medicament or placebo comprising a housing; locatable within said housing, a container having a dispensing aperture, wherein said container is movable relative to the housing to enable dispensing therefrom; and an actuation-indicator for detecting movement of the container relative to the housing, said actuation-indicator comprising a first part defining a pocket having an outlet therefrom and a second part movable relative to said first part to create a pressure change at said outlet.

In one aspect, said first and second parts jointly define a chamber and the second part comprises a flexible wall or membrane which is resiliently deformable to create said pressure change.

In another aspect said pocket of the first part is shaped for snug receipt of said second part to define a piston arrangement.

Suitably, the outlet is in communication with a pressure gauge to measure the pressure change. Preferably, the pressure gauge comprises a pressure transducer.

Suitably, the actuation-indicator additionally comprises a third part defining a second pocket having an outlet therefrom; and a pressure change channel for channelling airflow from the housing to the second pocket to create a pressure change at the outlet. This third part may be employed to monitor airflow through the housing of the dispenser. In a preferred aspect, the pressure change channel is at least partly foldable into the housing. The pressure change channel may comprise various grooves or tracks.

In one aspect, the actuation-indicator is mountable on the exterior of the housing. Suitably, the actuation-indicator comprises a carrier sleeve which is mountable on the exterior of the housing and separable therefrom. Preferably, the housing has a tubular portion, the container is movable within said tubular portion and said carrier sleeve is snugly receivable by the tubular portion.

One or more guide elements may be provided to the tubular portion and/or the carrier sleeve to guide the receipt of the carrier sleeve by the tubular portion. The guide elements may, for example, be mechanical guides such as tongue and groove arrangements. The guide elements may also for example, be visual guides such as colour coding arrangements.

A first end of the tubular portion may have a lip to prevent over-receipt of the carrier sleeve. The lip and the leading end of the carrier sleeve may be shaped for relative engagement.

The dispenser may additionally comprise a cap which is mountable on the container, wherein movement of the cap results in movement of the second part.

Suitably, the cap has a peg which engages said second part.

In another aspect, the actuation-indicator is mountable on the container.

Suitably, the container is an aerosol container. Preferably, the aerosol container provides measured doses.

Suitably, the dispenser is actuable in response to the breath of a user.

According to another aspect of the present invention there is provided a system for training users in the operation of a dispenser comprising a dispenser as described above in communication with a unit capable of visually or audibly indicating actuation of the dispenser. The unit may also be configured to enable visual or sound indication of the pressure profile associated with the inhalation pattern of the patient and the degree of synchronisation between the actuation and inhalation profiles.

According to a further aspect of the present invention there is provided the use of a system described above for training the user in the operation of the dispenser.

According to another aspect of the present invention there is provided an actuation-indicator for use with a dispenser comprising a housing and a container which is movable relative to said housing, said actuation-indicator comprising a first part defining a pocket having an outlet therefrom and a second part movable relative to said first part to create a pressure change at said outlet.

In one aspect, said first and second parts jointly define a chamber and the second part comprises a flexible wall which is resiliently deformable to create said pressure change.

In another aspect, said pocket of the first part is shaped for snug receipt of said second part to define a piston arrangement.

According to a further aspect of the present invention there is provided a kit of parts comprising an actuation-indicator as described above and a dispenser comprising a housing and a container which is movable relative to said housing. The kit of parts can also comprise means for connecting the actuation-indicator to an information processor such as a computer. The information processor typically comprises a multi-media display and is controllable by suitable software.

The dispenser may be used for dispensing medicament or placebo.

BRIEF DESCRIPTION OF THE SEVERAL VIEW OF THE DRAWINGS

A dispenser according to the invention will now be described with reference to the accompanying drawings in which.

DETAILED DESCRIPTION

Figure 1:
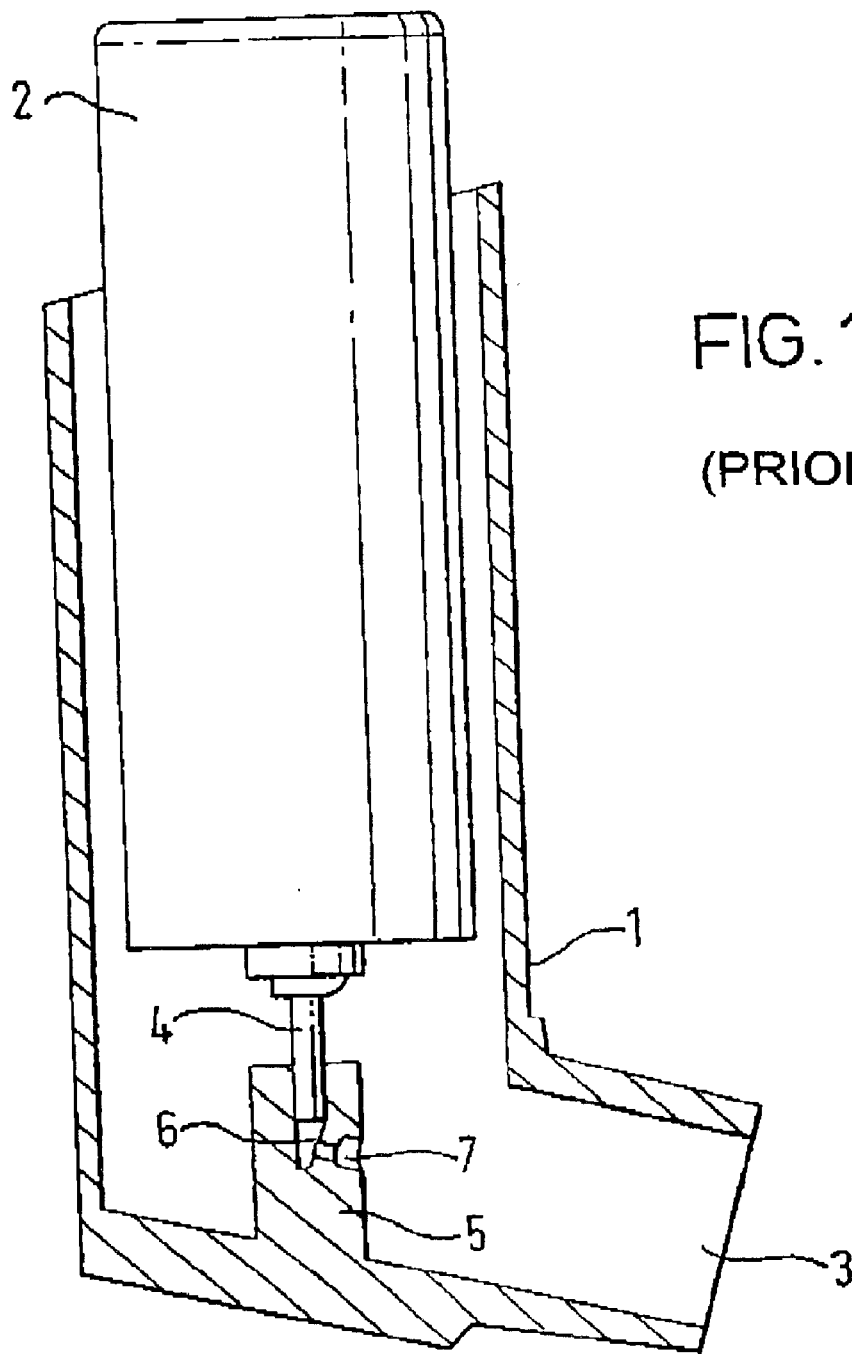
FIG. 1 is a sectional view of a known dispensing device.

The standard metered dose inhaler shown in FIG. 1 comprises a tubular housing 1 in which an aerosol container 2 can be located. The housing is open at one end (which will hereinafter be considered to be the top of the device for convenience of description) and is closed at the other. An outlet 3 leads laterally from the closed end of the housing 1. In the embodiment illustrated, the outlet 3 is in the form of a mouthpiece intended for insertion into the mouth of the patient but it may, if desired, be designed as a nozzle for insertion into the patient's nostril.

The aerosol container 2 has an outlet valve stem 4 at one end. This valve member can be depressed to release a measured dose from the aerosol container or, alternatively, the valve stem 4 can be fixed and the main body of the container can be moved relative to the valve member to release the dose.

As shown clearly in FIG. 1, the aerosol container 2 is located in the housing 1 so that one end protrudes from its open top. Spacer ribs (not shown) may be provided inside the housing to hold the external surface of the container 2 spaced from the internal surface of the housing 1. A support 5 is provided at the lower end of the housing 1 and has a passage 6 in which the valve stem 4 of the aerosol container 2 can be located and supported. A second passage 7 is provided in the support 5 and is directed towards the interior of the outlet 3.

Thus, when the parts are in the positions shown In FIG. 1, the protruding portion of the aerosol container 2 can be depressed to move the container relative to the valve stem 4 to open the valve and a dose of medicament contained in the aerosol will be discharged through the passage 7 and into the outlet 3 from which it can be inhaled by a patient. One dose will be released from the aerosol container each time it is fully depressed.

Figure 2:
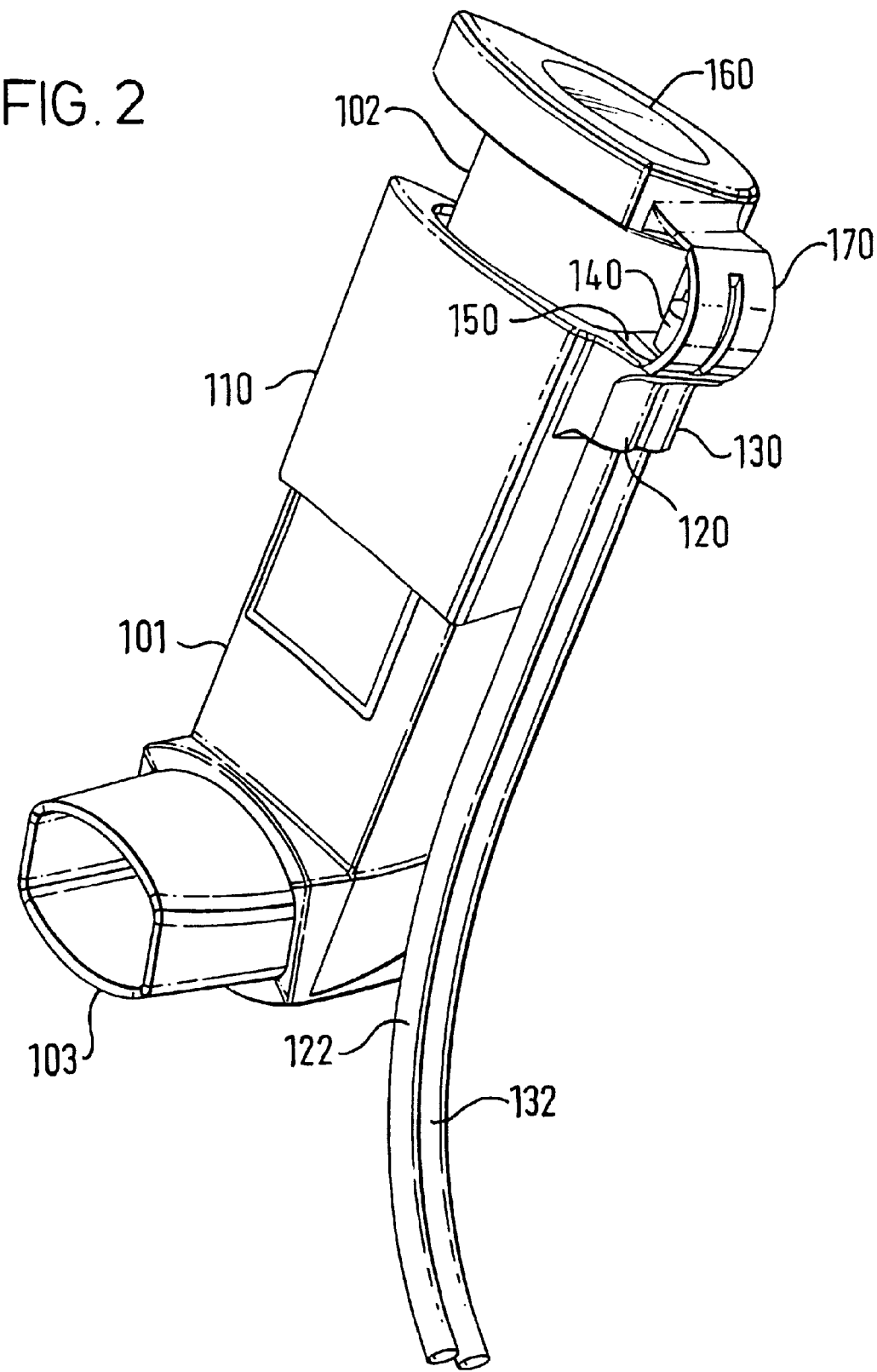
FIG. 2 is a perspective view of a dispenser in accord with the present invention.

FIG. 2 shows a standard metered dose dispenser (essentially identical to that shown in FIG. 1) incorporating an actuation-indicator in accord with the present invention. The metered dose inhaler comprises a tubular housing 101 containing an aerosol container 102 and having an outlet 103 in the form of a mouthpiece.

The actuation-indicator is seen to comprise a clip-on sleeve 110, which is sized and shaped to be snugly receivable by the exterior of the tubular housing 101 of the dispenser.

One side of the sleeve 110 is provided with two hollow cylinders 120, 130 from which respective hollow tubes 122, 132 protrude. The tubes 122, 132 may be separate tubes as shown, or in alternative embodiments the tubing may comprise multiple core or braided tubing. Each of the hollow tubes is in communication with a pressure transducer (not shown) for measurement of pressure changes. A deformable pressure button 140 is provided at the top end of the second hollow cylinder 130, thereby forming a chamber. A pressure change channel 150 is provided at the top end of the first hollow cylinder 120. A cap 160 is provided to the top of the aerosol container. The cap 160 is connected to the sleeve 110 by a strap 170.

Figure 3:
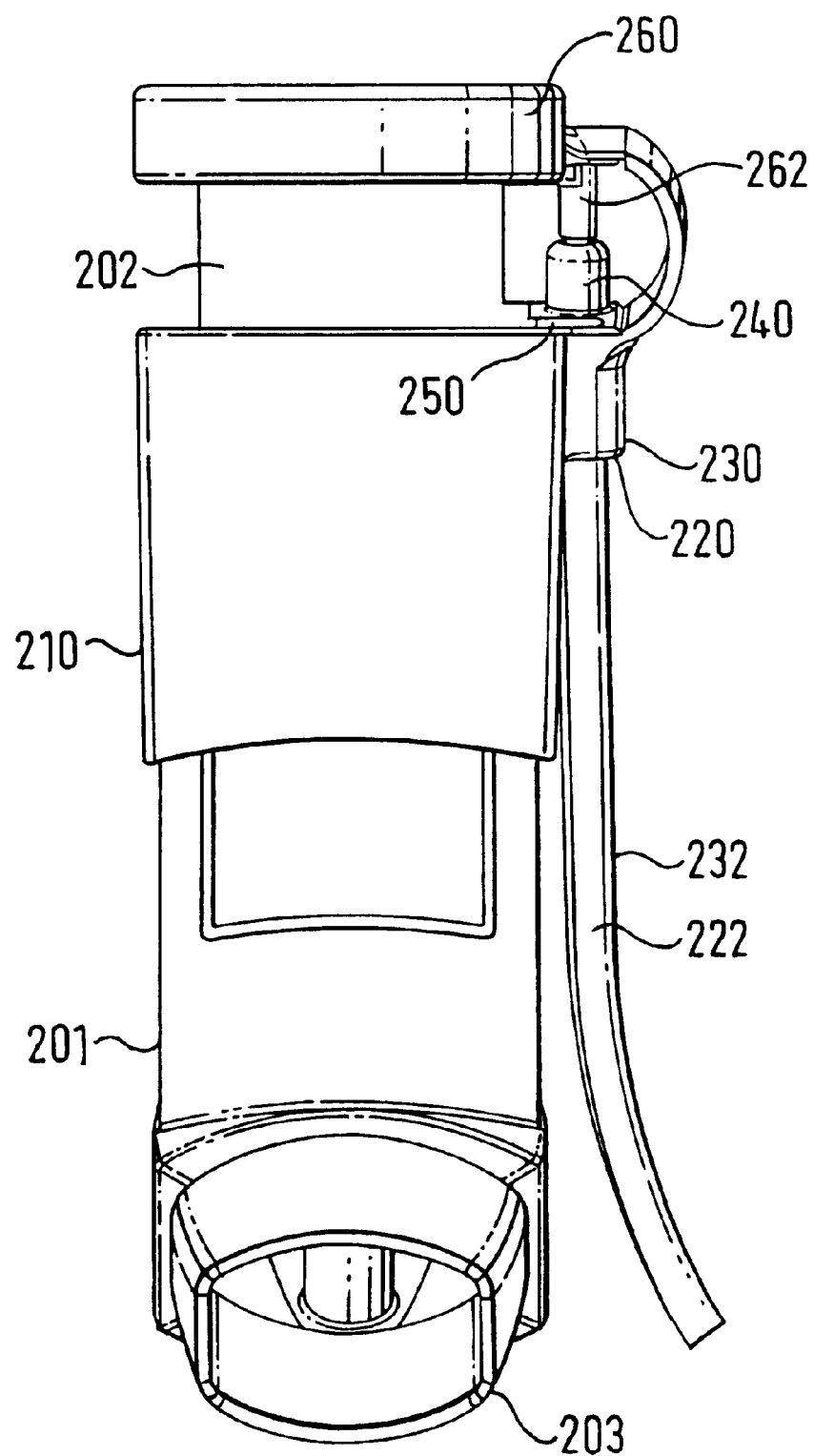
FIG. 3 is a front view of the dispenser of FIG. 2.

FIG. 3. shows a front view of the dispenser of FIG. 2. The cap 260 which connects to aerosol container 202 is seen to be provided with a peg 262 which engages the deformable button 240, located at the top end of the second hollow cylinder 230. Also Illustrated is pressure change channel 250 at the top end of first hollow cylinder 220. Hollow tubes 222 and 232 are attached to cylinders 220 and 230, respectively, and are in communication with a pressure gauge or transducer (not shown) for measurement of pressure changes.

Figure 4:
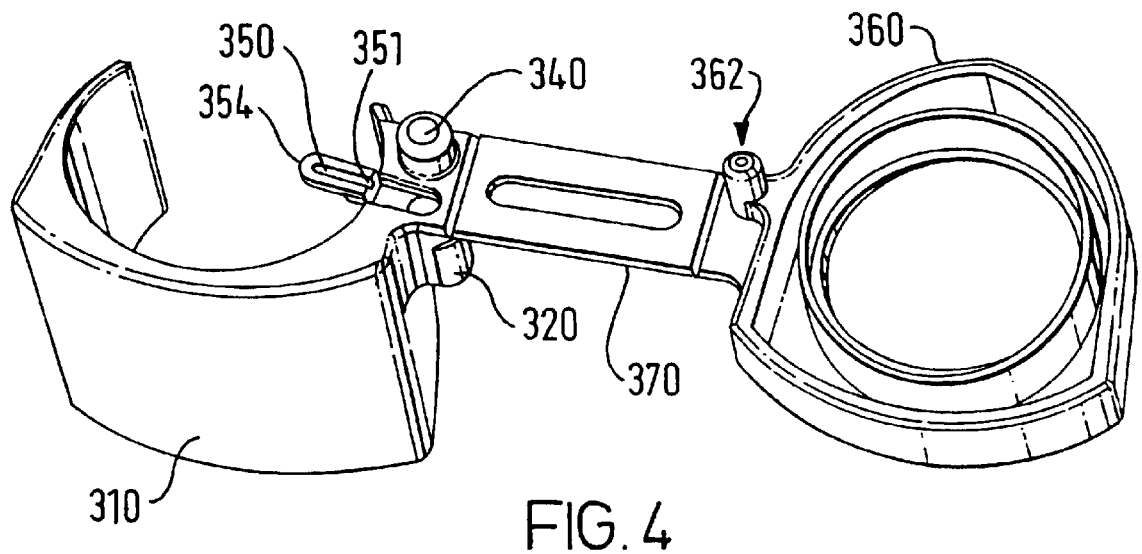
FIG. 4 is a perspective top view of an actuation-indicator in accord with the present invention.

FIG. 4 shows in more detail the actuation-indicator as employed with the dispenser in FIGS. 2 and 3. The pressure change channel 350 may be seen to comprise a slot 351 arrangement forming part of a foldable flap 354. The flap 354, which is pivotable on the inner rim of sleeve 310, can be folded shut (not shown) thereby partially closing the vertical channel through 320 and redirecting the channel horizontally along the length of slot 351. The change in pressure caused by flow into the housing 101, 201 of the inhaler, between the housing 101, 201 and the aerosol container 102, 202 can therefore be recorded at the end of the slot 351. As can be seen, the pressure change channel 350 communicates between the housing 101, 201 and the first hollow cylinder 320 thereby enabling measurement of any pressure change resulting from air flow through the housing at the outlet thereof. Also shown is the arrangement of the sleeve 310 relative to the cap 360, connected by means of strap 370. In the view shown, deformable pressure button 340 can be seen to be located opposite peg 362 such that they engage when sleeve 310 and cap 360 are affixed to the inhaler as in FIGS. 2 and 3.

Figure 5:
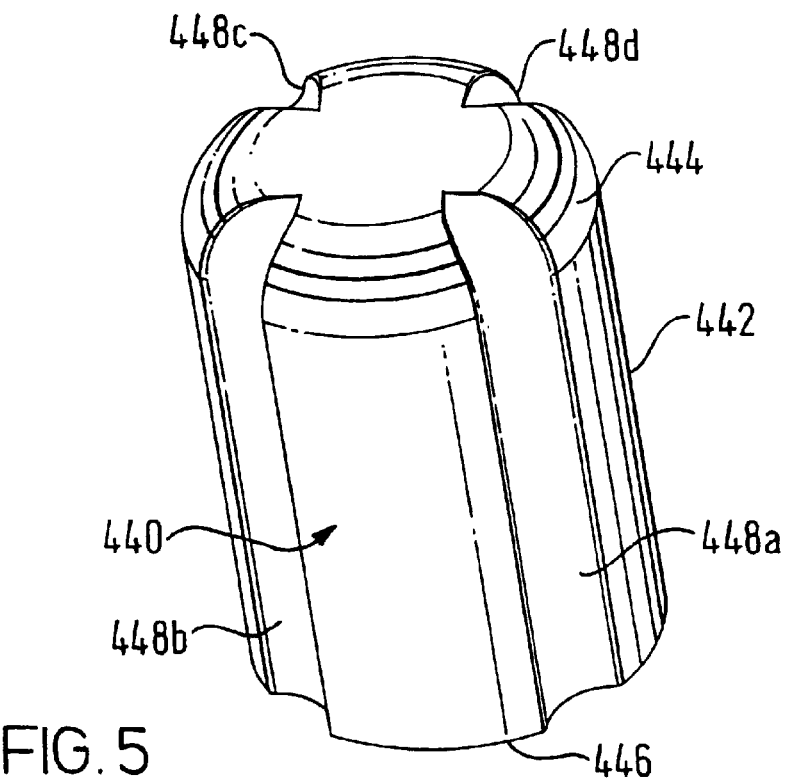
FIG. 5 is a perspective view of a deformable pressure button for use with the actuation-indicator of FIG. 4.

FIG. 5 shows the geometry of a deformable pressure button 440 which may be employed in the actuation-indicator of FIG. 4. The pressure button 440 may be seen to have an essentially cylindrical body 442, a rounded top end 444 and an open bottom end 446. The cylindrical body is provided with grooves 448a–d which are shaped such as to guide the uniform, downward deformation of button 440 when pressure is applied at the top end 444.

Other geometries of pressure button 440 are conceivable, including those featuring score lines, concertina folds and other groove forms wherein the overall geometry is selected to assist in the uniform, downward deformation of the button 440. The pressure button 440 is wholly or partly comprised of a flexible material, such as a synthetic polymeric material or rubber.

On actuation of the dispenser of FIGS. 2 and 3 by a patient, the aerosol container 102, 202 is moved into the housing 101, 201. The cap 160, 260 on the aerosol container is therefore moved towards the sleeve 110, 210. The peg, 262 on the cap 160, 260 is hence also pushed into the button 140, 240 which deforms causing a pressure change in the second cylinder 130, 230 and tube 132, 232. The pressure change is measurable by a pressure transducer (not shown).

In an alternative embodiment herein the peg 262 and pressure button 140, 240 arrangement may be replaced by a piston arrangement in which for example, a cylindrical peg on the cap is snugly received by a cylindrical pocket on the sleeve to form a piston. Movement of the cylindrical peg into the cylindrical pocket thus causes a pressure change in much the same way as engagement of the peg 262 with the pressure button 140, 240 causes a pressure change.

Typically, actuation of the dispenser will be coordinated with the taking of an inward breath by the patient. This inward breath causes a pressure change inside the housing 101, 201 of the dispenser and in the pressure change channel 150, 250 and thus, also in the first cylinder 120, 220 and tube 122, 222. This further pressure change is measurable by a second pressure transducer (not shown).

A still further tube may also be provided to the dispensers of FIG. 2 and FIG. 3 for the measurement by connection to a third pressure transducer (not shown) of the pressure profile on propelled release of medicament or placebo from the aerosol container 102, 202. Subtracting therefrom the profile obtained from the second pressure transducer allows for the provision of a flat baseline for the release profile even in the presence of a pressure fluctuations resulting from the patients' inhalation through the mouthpiece 103, 203. Alternatively, a differential pressure sensor could be used to subtract one pressure measurement from the other.

Figure 6:
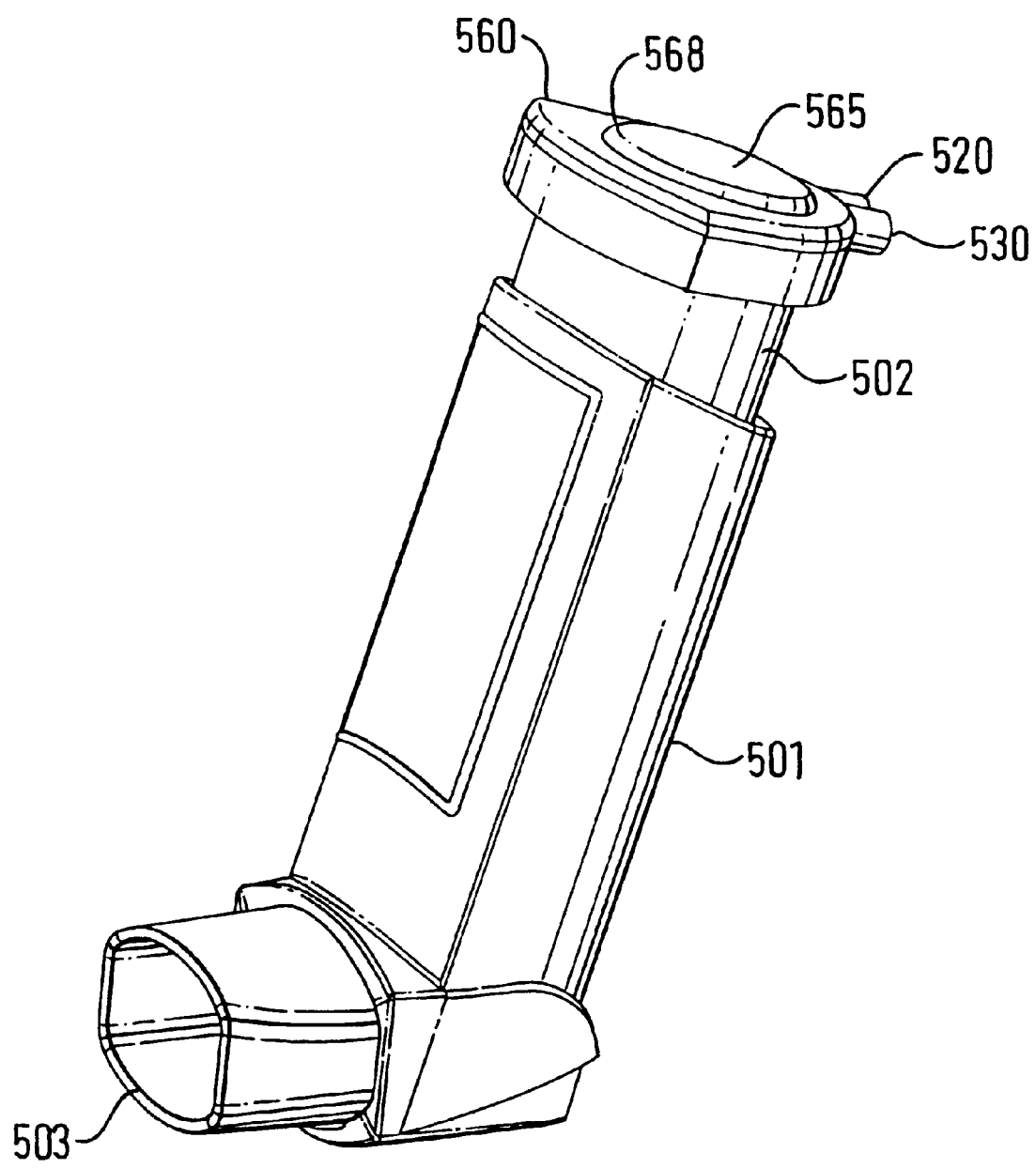
FIG. 6 is a perspective view of a second dispenser in accord with the present invention.

FIG. 6 shows a standard metered dose dispenser (essentially identical to that shown in FIG. 1) incorporating an actuation-indicator in accord with the present invention. The metered dose inhaler comprises a tubular housing 501 containing an aerosol container 502 and having an outlet 503 in the form of a mouthpiece.

Figure 7A:
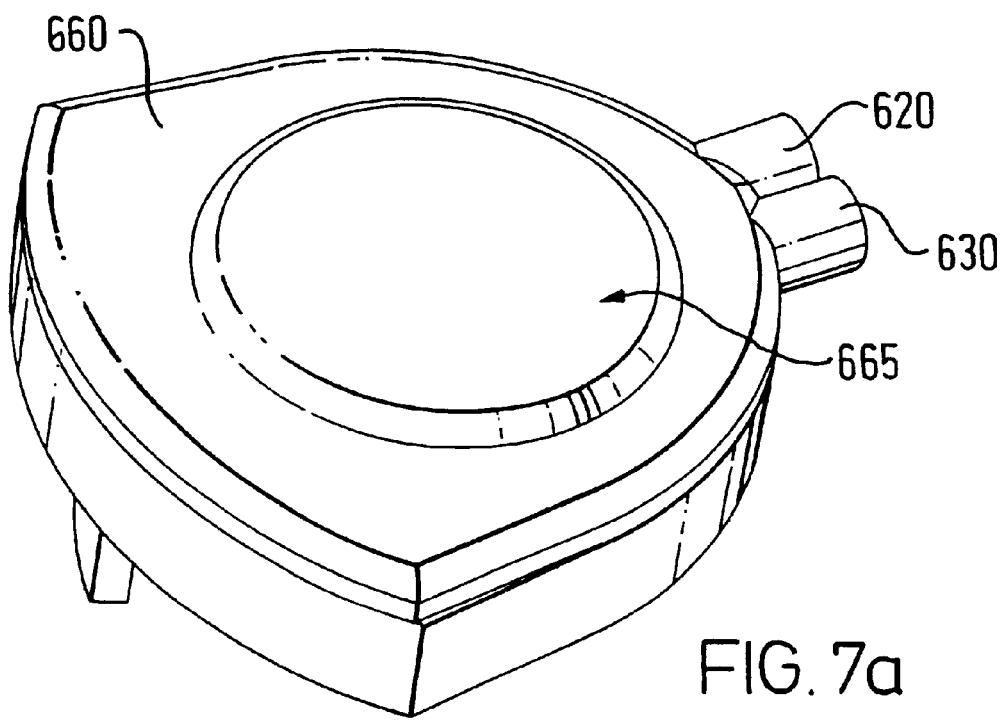
FIGS. 7a and 7b are perspective views of the outer and inner parts of a second actuation-indicator in accord with the present invention.
Figure 7B:
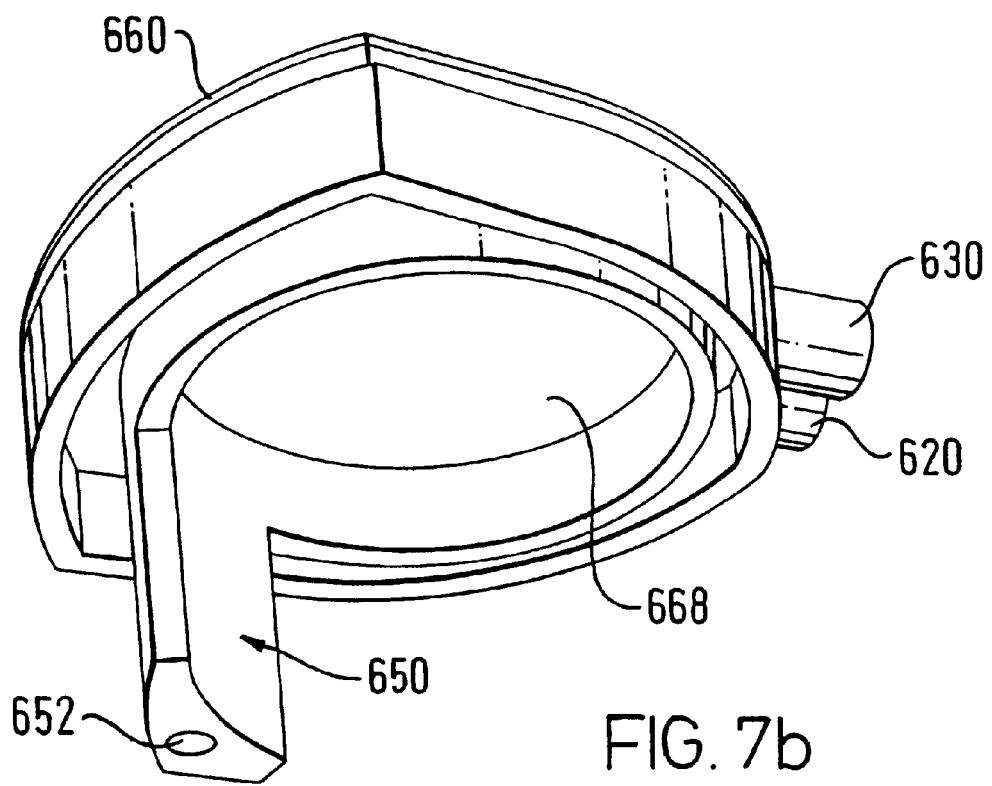

The actuation-indicator which is shown in more detail in FIGS. 7a and 7b is seen to comprise a cap 660, which is sized and shaped to be snugly receivable by the top end of the aerosol container 502 (FIG. 6). The cap 660 is provided with a flexible membrane 665 which forms part of a thin flat cylindrical chamber 668. The chamber 668 has an outlet 630 which is shaped for receipt of tubing (not shown) which may be connected to a pressure gauge (not shown). The cap 660 is also provided with a pressure change channel 650 having an inlet 652 which is receivable in the dispenser between the aerosol container 502 and the housing 501 (FIG. 6). The pressure change channel 650 itself has an outlet 620 which is shaped for receipt of tubing (not shown) and may be connected to a second pressure gauge (not shown).

On actuation of the dispenser of FIG. 6, the aerosol container 502 is pushed into the housing 501 by the thumb action of a patient. The patient's thumb also pushes flexible membrane cap 565 inwardly causing an increase of pressure in the chamber 568 and at outlet 530. This increase of pressure change is measurable by a pressure transducer (not shown).

Typically, actuation of the dispenser of FIG. 6 will be coordinated with the taking of an inward breath by the patient. This inward breath causes a pressure change inside the housing 501 of the dispenser and in the pressure change channel 650 and at outlet 620. This further pressure change is measurable by a second pressure transducer (not shown).

Figure 8:
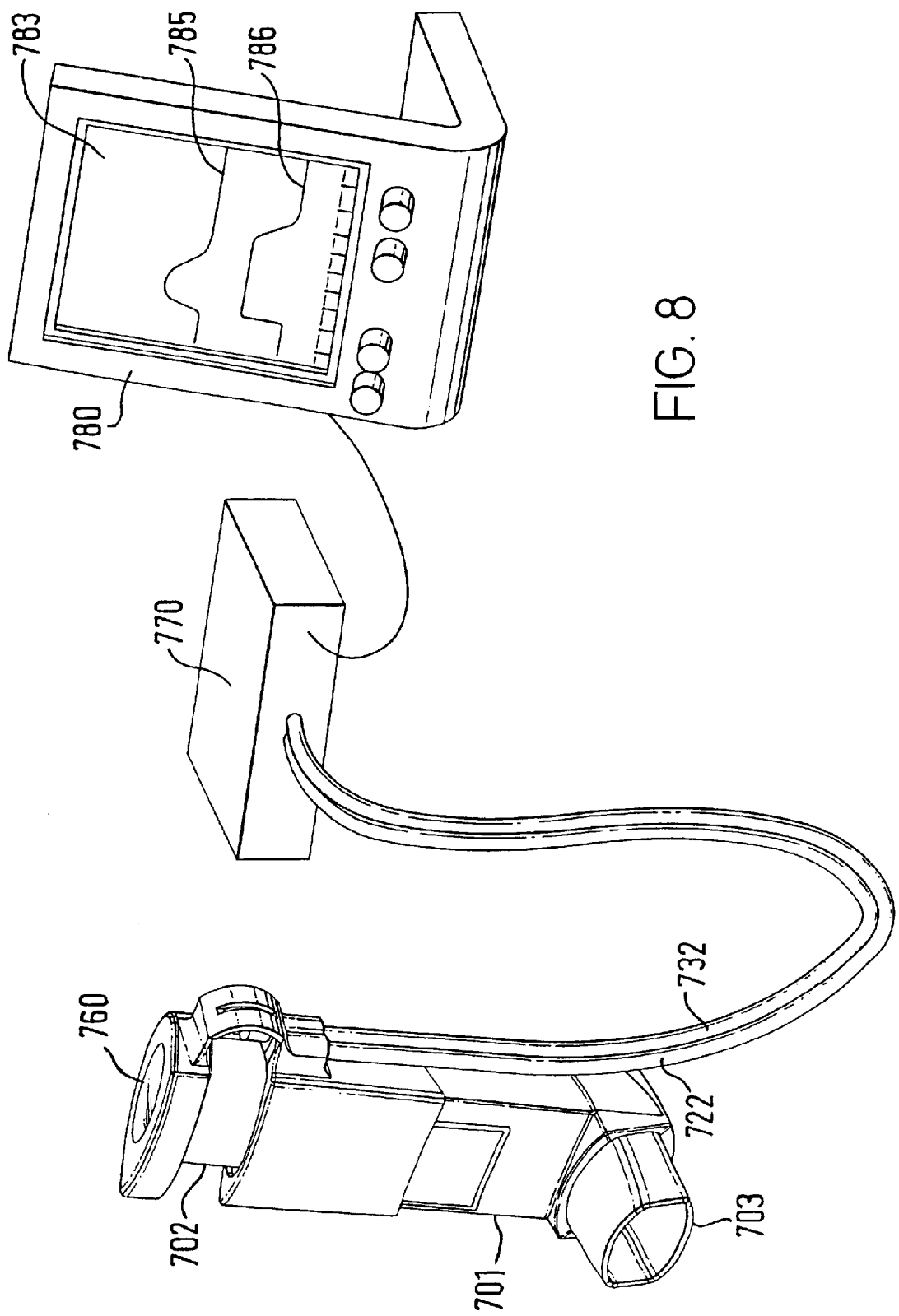
FIG. 8 is a perspective view of a training system in accord with the present invention.

The use of visual display means is of particular utility in the training of patients in the correct operation of the dispenser, since the actuation profile, inhalation profile and release profile may be visually represented. FIG. 8 shows a suitable training system in which the dispenser is connected via tubing 722, 732 to processing means 770 which comprises pressure transducers (not shown). The processing means 770 are in turn connected to a visual display unit 780 having a display screen 783 on which are represented traces for the inhalation 785 and actuation 786 profiles. The processing means 770 may include means for recordal and playback of particular profiles. The visual display unit 780 may be arranged to display graphical or cartoon images for training of the patient.

The use of electronic computational and storage means is of particular utility in the comparison of pressure release profiles of different dispensers Whilst the present invention has been described in detail in respect of a metered dose inhaler actuatable manually by the patient it will be appreciated that other actuation mechanisms can be substituted. In particular, the use of a breath-operated inhaler in which the actuation is assisted, and is responsive to, preferably triggered by, the inward breath of the patient, is also envisaged.

The dispenser of the invention is suitable for dispensing medicament, particularly for the treatment of respiratory disorders. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti- inflammatories, e.g., beclomethasone dipropionate, fluticasone propionate, flunisolide, budesonide, rofleponide, mometasone furoate, ciclesonide or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol or 4-hydroxy-7-[2-[[2-[[3-(2-phenylethoxy) propyl] sulfonyl] ethyl] amino] ethyl-2(3H)-benzothiazolone; diuretics, e.g., amiloride; anticholinergics, e.g., ipratropiumn, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies.

It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferred medicaments are selected from albuterol, salmeterol, ipratropium bromide, fluticasone propionate and beclometasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an antiinflammatory steroid such as a beclomethasone ester (e.g., the dipropionate) or a fluticasone ester (e.g., the propionate). A particularly preferred combination comprises salmeterol xinafoate salt and fluticasone propionate.

It may be appreciated that any of the parts of the metered dose inhaler which contact the medicament suspension may be coated with materials such as fluoropolymer materials which reduce the tendency of medicament to adhere thereto. Suitable fluoropolymers include polytetrafluoroethylene (PTFE) and fluoroethylene propylene (FEP). Any movable parts may also have coatings applied thereto which enhance their desired movement characteristics. Frictional coatings may therefore be applied to enhance frictional contact and lubricants used to reduce frictional contact as necessary.

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. A dispenser for dispensing medicament or placebo comprising a housing; locatable within said housing, a container having a dispensing aperture, wherein said container is movable relative to the housing to enable dispensing therefrom; and an actuation-indicator for detecting movement of the container relative to the housing, said actuation-indicator comprising a first part defining a pocket having an outlet therefrom and a second part movable relative to said first part to create a pressure change at said outlet.

2. A dispenser according to claim 1, wherein said first and second parts jointly define a chamber and the second part comprises a flexible wall or membrane which is resiliently deformable to create said pressure change.

3. A dispenser according to claim 1, wherein said pocket of the first part is shaped for snug receipt of said second part to define a piston arrangement.

4. A dispenser according to claim 1, wherein the outlet is in communication with a pressure gauge to measure the pressure change.

5. A dispenser according to claim 4, wherein the pressure gauge comprises a pressure transducer.

6. A dispenser according to claim 1, wherein the actuation-indicator additionally comprises a third part defining a second pocket having an outlet therefrom; and a pressure change channel for channelling airflow from the housing to the second pocket to create a pressure change at said outlet.

7. A dispenser according to claim 6, wherein said pressure change channel is at least partly foldable into the housing.

8. A dispenser according to claim 1, wherein the actuation-indicator is mountable on the exterior of the housing.

9. A dispenser according to claim 8, wherein the actuation-indicator comprises a carrier sleeve which is mountable on the exterior of the housing and separable therefrom.

10. A dispenser according to claim 9, wherein the housing has a tubular portion, the container is movable within said tubular portion and said carrier sleeve is snugly receivable by the tubular portion.

11. A dispenser according to claim 1, additionally comprising a cap which is mountable on the container wherein movement of the cap results in movement of the second part.

12. A dispenser according to claim 11, wherein the cap has a peg which engages said second part.

13. A dispenser according to claim 1, wherein the actuation-indicator is mountable on the container.

14. A dispenser according to claim 1, wherein the container is an aerosol container.

15. A dispenser according to claim 14, wherein the aerosol container provides measured doses.

16. A dispenser according to claim 1, wherein the dispenser is actuable in response to the breath of a user.

17. A system for training users in the operation of a dispenser comprising:
   (a) a dispenser for dispensing medicament or placebo comprising a housing; locatable within said housing a container having a dispensing aperture, wherein said container is movable relative to the housing to enable dispensing therefrom; and an actuation-indicator for detecting movement of the container relative to the housing, said actuation-indicator comprising a first part defining a pocket having an outlet therefrom and a second part movable relative to said first part to create a pressure change at said outlet, and (b) an indicator unit, said indicator unit being in communication with said dispenser and said indicator unit being capable of visually or audibly indicating actuation of the dispenser.

18. Use of a system for training users in the operation of a dispenser comprising:

(a) providing a system according to claim 17;

(b) actuating said dispenser, and (c) monitoring said actuator-indicator to determine when correct operation of said device has occurred.

19. Use of a dispenser for dispensing medicament or placebo comprising:

(a) providing a dispenser comprising a housing; locatable within said housing, a container having a dispensing aperture, wherein said container is movable relative to the housing to enable dispensing therefrom; and an actuation-indicator for detecting movement of the container relative to the housing, said actuation-indcator comprising a first part defining a pocket having an outlet therefrom and a second part movable relative to said first part to create a pressure change at said outlet; and (b) actuating said dispenser to dispense a dose of medicament or placebo.

* * * * *